(12) United States Patent  
Unkelbach et al.

(10) Patent No.: US 9,714,200 B2  
(45) Date of Patent: Jul. 25, 2017

(54) PROCESS FOR PREPARING ETHYLENE AND OTHER OLEFINS FROM AQUEOUS SOLUTIONS OF THE CORRESPONDING ALCOHOLS

(71) Applicant: Fraunhofer-Gesellschaft zur Foerderung der angewandten Forschung e.V., Munich (DE)

(72) Inventors: Gerd Unkelbach, Leipzig (DE); Rainer Schweppe, Karlsruhe (DE); Thomas Hirth, Buehl (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 168 days.

(21) Appl. No.: 14/373,080

(22) PCT Filed: Jan. 24, 2013

(86) PCT No.: PCT/EP2013/051367  
§ 371 (c)(1),  
(2) Date: Jul. 18, 2014

(87) PCT Pub. No.: WO2013/110723  
PCT Pub. Date: Aug. 1, 2013

(65) Prior Publication Data  
US 2014/0364670 A1    Dec. 11, 2014

(30) Foreign Application Priority Data  
Jan. 24, 2012   (DE) .................. 10 2012 200 996

(51) Int. Cl.  
*C07C 1/22* (2006.01)  
*C07C 1/24* (2006.01)

(52) U.S. Cl.  
CPC .............. *C07C 1/22* (2013.01); *C07C 1/24* (2013.01); *C07C 2521/04* (2013.01); *C07C 2521/06* (2013.01); *Y02P 20/544* (2015.11)

(58) Field of Classification Search  
CPC .................................. C07C 1/20; C07C 1/22  
(Continued)

(56) References Cited

U.S. PATENT DOCUMENTS

| | | |
|---|---|---|
| 134,926 A | 1/1873 | Pilkington |
| 2011/0098519 A1 | 4/2011 | Ramesh et al. |
| 2011/0105815 A1 | 5/2011 | Minoux et al. |

FOREIGN PATENT DOCUMENTS

| | | |
|---|---|---|
| GB | 576480 | 4/1946 |
| GB | 587378 | 4/1947 |

(Continued)

OTHER PUBLICATIONS

Anikeev, et al., "Kinetics and thermodynamics of 2-propanol dehydration in supercritical water," The Journal of Supercritical Fluids, 32:123-135, 2004.

(Continued)

*Primary Examiner* — Sharon Pregler  
(74) *Attorney, Agent, or Firm* — Duane Morris LLP

(57) ABSTRACT

The invention relates to a process for the continuous production of one or more olefins from an aqueous solution of corresponding alcohol(s) including: Providing a solid-free aqueous solution of the alcohol(s); putting the solution through a reactor, which is filled with a fixed-bed catalyst such that the solution comes into contact with the catalyst when flowing through the reactor at a temperature of at least 300° C. and a pressure of at least 220 bar in such a temperature/pressure combination that the alcohol(s) are reacted under supercritical conditions; and transferring a resulting two-stage mixture to a separator, in which the (Continued)

mixture is separated in a raw olefin gas phase and an aqueous liquid phase; wherein the catalyst is selected from among metal oxides having the properties of a Bronstedt acid, insoluble metallic or semi-metallic phosphates as well as porous materials selected from among pumice and carbon, the surface area of which is coated with inorganic acid groups.

19 Claims, 2 Drawing Sheets

(58) Field of Classification Search
USPC .............................. 585/638, 639, 640, 641
See application file for complete search history.

(56) References Cited

FOREIGN PATENT DOCUMENTS

| WO | 2007003899 A1 | 1/2007 |
|---|---|---|
| WO | 2007003901 A1 | 1/2007 |
| WO | 2007003910 A1 | 1/2007 |
| WO | 2009022990 A1 | 2/2009 |
| WO | 2009098269 A1 | 8/2009 |
| WO | 2011115656 A1 | 9/2011 |

OTHER PUBLICATIONS

Aras, et al., "Reaktionstechnische Untersuchungen zur Ethylenherstellung aus wässrigen Ethanollösungen (Fermenteausträgen)—Eine nachhaltige Alternative zum Steam-Cracker," Technische Universität Darmstadt, 2011.

Vogel, "Nah—und überkritische Fluide zur Defunkitionali-sierung von Mono—und Polyalkoholen," Chemie Ingenieur Technik, 83, No. 9:1-10, 2011.

Halvorsen, et al., "Process Optimization for the Supercritical Dehydration of Ethanol to Ethylene," AIChE National Meeting, Chicago 1990.

Watanabe, et al., "Conversions of some small organic compounds with metal oxides in supercritical water at 673 K†," Green Chemistry, 5:539-544, 2003.

Ramayya, et al., "Acid-catalysed dehydration of alcohols in supercritical water," FUEL, 66:1364-1371, 1987.

Xu, et al., "Mechanism and kinetics of the acid-catalyzed formation of ethene and diethyl ether from ethanol in supercritical water," Ind. Eng. Chem. Res., 30 (7):1478-1485, 1991.

Xu, et al., "Mechanism and Kinetics of the Acid-Catalyzed Dehydration of Ethanol in Supercritical Water†", The Journal of Supercritical Fluids, 3:228-232, 1990.

Peterson et al., "Thermochemical biofuel production in hydrothermal media: A review of sub- and supercritical water technologies", Energy & Environmental Science, 2008, 1, 32-65.

Nouri et al., Supercritical Water Ethanol Reforming for Hydrogen Production: (Effect of Different Support on Nickel Based Catalyst in Supercritical Water Condition), Asian Journal of Chemistry, vol. 22, No. 1 (2010), pp. 569-581.

Watanabe et al., Conversions of some small organic compounds with metal oxides in supercritical water at 673 K, Green Chemistry, 2003, 5, pp. 539-544 (Presented at The First International Conference on Green & Sustainable Chemistry, Tokyo, Japan, Mar. 2003).

Ramayya et al., Acid-catalysed dehydration of alcohols in supercritical water, Fuel, vol. 66, Oct. 1987.

PROCESS FOR PREPARING ETHYLENE AND OTHER OLEFINS FROM AQUEOUS SOLUTIONS OF THE CORRESPONDING ALCOHOLS

The invention relates to a process for producing ethylene and, potentially, other olefins from aqueous solutions of corresponding alcohols in a condensed phase using a heterogeneous catalyst. Said process is particularly suited for continuously operated reactor systems.

Prior to 1945, the majority of ethylene production was based on the dehydration of ethanol in the gas phase of heterogeneous catalysts. The reaction was conducted in fluidized bed reactors at 350-400° C.; the contact times between said catalyst and reactant was 1-10 seconds. "Acidic" solids, e.g. silica aluminum oxide catalysts or various zeolites were used as catalysts. The yields were at 99% (US 134,926) and selectivity was at 98%. Steam cracking of relatively cost-efficient hydrocarbons later became the method of choice.

In 1944, a suggestion was made for the catalytic dehydration of ethanol at temperatures exceeding 250° C. and any high pressures (GB 587,378). Phosphoric acid, concentrated sulfuric acid, γ-aluminum oxide, and sodium carbonate were designated as possible catalysts; the only embodiment example shows the reaction of alcohol in the presence of 5% phosphoric acid in a batch process. After separating the water that develops during the reaction, the formed ethylene is sufficiently pure for a variety of—unspecified—purposes.

Today, the dehydration of ethanol is gaining renewed interest because ethanol accumulates through the fermentation of biomass. However, gas phase dehydration is hardly considerable for this because pure ethanol is necessary for that, which is why the water has to be removed from the fermenter solution through rectification and subsequently removed from the azeotrope. The expenditure of energy and costs for such a process is so high that it is considered to be an unrealistic alternative in most industrial nations.

A process for producing olefins, including primarily ethylene, is described in WO 2007/003899 A1, WO 2007/003901, and WO 2007/003910 A1, which allows for the presence of up to 50% of water by weight. In the case of high water contents, e.g. in the case of unprocessed bio-alcohols, distillation should occur first in order to lower the water content. The intent is to react the output material with increased pressure and increased temperature, which are not characterized in further depth; alkenes and ethers emerge, which are then separated. The competition of the underlying reactions is discussed; too small of an amount of ethylene could be compensated for through a combination of reaction and distillation. Equally heterogeneous and homogenous catalysts are suggested as catalysts, including zeolites, sulfonated carriers, sulfuric and phosphoric acid. Heteropoly acids are stated as preferable. In the one example, an 80% aqueous ethanol solution is subjected to reactive distillation without a catalyst.

For ethanol dehydration, WO 2011/115656 determines that the alteration of the used catalyst from a pure aluminum oxide to aluminum oxide in a mixture with yttrium oxide decreases the occurrence of oxygenated products and that easily separable $CO_2$ primarily arises among these products, while the formation of acetaldehyde is below the detection limit.

There is a variety of studies of the reaction of propanol in supercritical water. In Green Chemistry, 2003(5), 539-544, M. Watanabe et al. present results that were achieved when using catalysts. Accordingly, sulfuric acid promotes the formation of propylene from 2-Propanol, while the formation of acetone is preferred in the presence of NaOH and no propylene develops at all. Propylene always developed with various metal oxides as catalysts, which is why the authors expect acidic centers of these materials in supercritical water. However, the yield was very different from oxide to oxide; in addition, acetone also developed with $ZrO_2$ and $TiO_2$ (the measurements occurred primarily after 15 minutes of reaction time). The detected specificity was comparable for sulfuric acid and most of the used oxides and was at approx. 70 mol %. V. I. Anikeev et al. studies the kinetic and thermodynamic reaction of 2-Propanol (The Journal of Supercritical Fluids 32, 123-135 (2004)), though only with respect to the influence of the density of the reaction medium.

While propanol can be transferred in supercritical water relatively easily, the analogous reaction with ethanol is not readily successful. The summary contribution of G. Herbert Vogel in Chemie Ingenieur Technik 2011, 83, p. 1-9, designates this alcohol as the "hardest nut to crack". In this regard, the problem lies partially in the minimal reaction yields and partially in the minimal specificity. Xiadong Xu et al. studied the dehydration of ethanol with various concentrations of alcohol in water, various sulfuric acid concentrations, and various retention times (The Journal of Supercritical Fluids, 1990(3), 228-232; Ind. Eng. Chem. Res. 30(7), 1991, 1478-1485). The results show that although the dehydration of ethanol in the presence of sulfuric acid should have a high specificity, the yields were unsatisfactory. S. Ramayya et al. achieved comparable results in FUEL 66 (1987), 1364-1371; with the results presented by this group, we see that the carbon balance in the experiment could only be closed by 88% although no byproducts were detected. With an increase of the ethanol concentration in the influx to the reaction, the ethylene yield increases accordingly only slowly, while the formation of diethyl ether strongly increases. Thus, for improving the balance, literary resources suggest returning the developed ether to the reactor in the case of high ethanol concentrations (Halvorsen et al. in Process Optimization for the Supercritical Dehydration of Ethanol to Ethylene in AIChE National Meeting, Chicago, 1990).

As a catalyst, sulfuric acid as well as aluminum sulfate in many cases is corrosive; the effected container walls can then for their part develop catalytic activity, as G. Aras et al. were able to demonstrate in a final report for the Max-Buchner Research Foundation in January 2011 entitled, "Reaction Engineering Studies for the Production of Ethylene from Aqueous Ethanol Solutions (Fermenter Discharge)—A Sustainable Alternative to Steam Cracking" (Technical University of Darmstadt). The yields with various other homogenous catalysts determined by this group were never over 10%; particularly zinc sulfate, which catalyzes the dehydration of propanol to propene very effectively, proved to be unsuitable. This confirms the assumption that ethanol is the most difficult to dehydrate due to the less stable carbocation. An increase of temperatures or retention times beyond those studied is not shown because the gasification reaction to synthesis gas would then begin to dominate.

In summary, the present state of the art for the dehydration of alcohols in supercritical water allows for the conclusion that (a) liquid acids as catalysts are difficult to monitor due to the competing reaction on the container wall and (b) the dehydration of ethanol cannot be compared with that of higher alcohols because the yields, and particularly the specificities, are significantly better with higher acids due to the various electronic situation in the transition states. The purely speculative claims of the other printed publication GB 587 378 and the contrasting results of newer studies incidentally leave the expert without a clear picture.

The object of the invention is to find a process capable of being continuously conducted, with which the respective alkylene(s) can be obtained cost-efficiently and easily from alcoholic aqueous solution even of a minimal concentration, and particularly those containing ethanol, through dehydration, wherein said process should enable in particular a high specificity of dehydration in relation to competitive reactions. The development of residues that can be disposed of exclusively in an environmentally friendly manner is also strived for.

To solve the problem, the inventors propose a process under reaction conditions above the critical point of water, namely by using a fixed-bed catalyst with specific properties. The selection of the fixed-bed catalyst allows the process to be easily conducted, regardless of the type of alcohol, and thus, the use of the process for the dehydration of ethanol as well. The fixed-bed catalyst, which is arranged in a suitable reactor, can be perfused with large amounts of raw material. Said raw material is an aqueous or aqueous alcoholic solution, e.g. from biomass that can be particularly fermented. Due to the fact that only a solid catalyst is used, and therefore no liquid or dissolved acid gets in the reacted solution or solution, which is to be reacted, separation steps or other purifications of the product stream are not necessary and the residue has a pH value that enables environmentally-friendly disposal without further measures.

BRIEF DESCRIPTION OF THE DRAWINGS

Embodiments of the invention will now be described by way of example with reference to the accompanying drawings.

Figure 1:
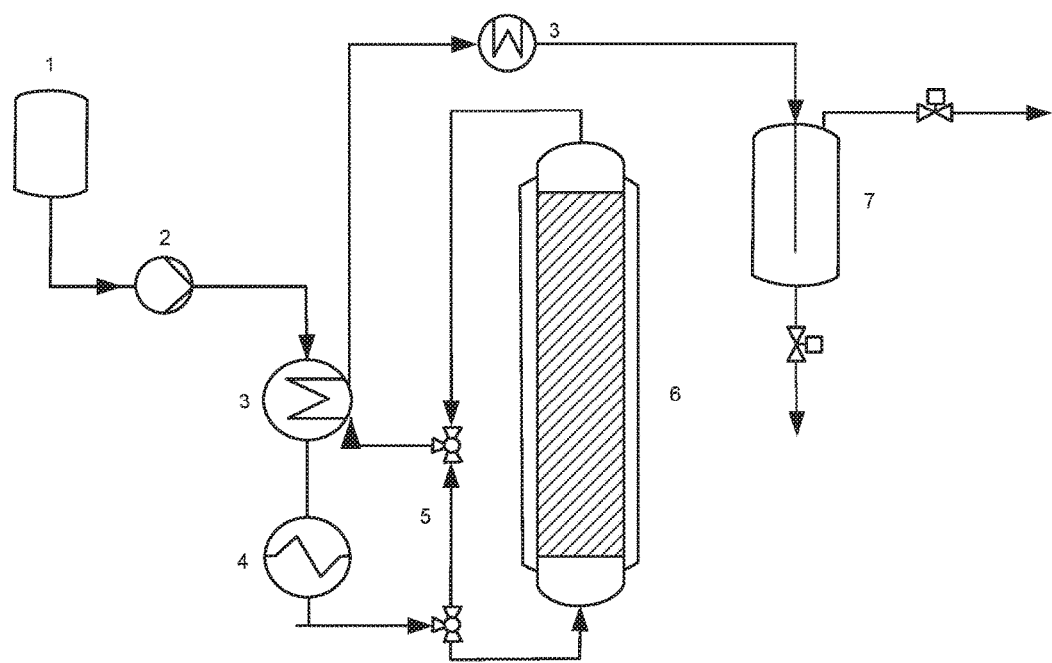
FIG. 1 is a system diagram illustrating the preferred progression of the reaction in accordance with the present invention.

Surprisingly, the inventors found that the fixed-bed catalysts provided for the process enable very high yields when selecting suitable, relatively short retention times with almost no secondary reactions. In supercritical areas, yields of nearly 95% can be achieved with an almost complete specificity. The reason for this could be that very high diffusion rates can be achieved due to the low viscosity of the reaction mixture with a simultaneously prevailing, enormously high density in the supercritical state. This enables a high space/time yield, which leads to higher productivity (or enables the reduction of the reactor volume). Under supercritical conditions, water also has positive solution properties for non-polar substances, such as olefins, because the relative dielectric constant decreases substantially. Thus, the inventors assume—without desiring to be limited to this—that reactants, the intermediate stages of the reaction, and the resulting olefins are always in a homogenous, condensed phase and no inhibition of diffusion occurs. Only this state enables the use of substantially aqueous reactants as strived for by the invention.

Metal oxides that behave like Brønstedt acids, i.e. proton donors, and including particularly those, the surface of which has been modified with acid groups, are suitable as catalysts for this process. Furthermore, insoluble metallic or semi-metallic phosphates, and materials having a high specific surface area, which are coated with inorganic acid molecules, provided that these materials are not affected by the environmental conditions prevailing during the reaction. Experts are aware of these; suitable examples are modified pumice and modified activated carbon, although no zeolite materials.

In principle, all oxides are suitable as metal oxides provided that they, as defined above, have the properties of a Brønstedt acid, and including particularly those of the $3^{rd}$ primary group and the $4^{th}$-$6^{th}$ subgroup (transition elements) of the periodic table as well as oxides of elements from the group of lanthanides, e.g. cerium. This preferably includes oxides of the $3^{rd}$ main group as well as acid-modified metal oxides, and in turn the latter including oxides of the elements of the $3^{rd}$ main group and the $4^{th}$-$6^{th}$ subgroup (transition elements) of the periodic table. Particularly sulfate or phosphate groups are suitable as acid groups. For example, oxides of aluminum, zirconium or titanium, the surface of which is coated with acid groups, or porous materials such as pumice or carbon, particularly activated carbon, the surface of which is covered with acid groups, are suitable. These materials in turn are particularly preferably coated with sulfate or phosphate groups.

It should be noted that the term "metal oxides" in the present case is intended to include both unmodified and modified materials (e.g. with acid groups).

The process is particularly suited for the reaction and, thus, the utilization of ethanol, although is not limited to this, as it is also naturally suitable for the reaction of higher alcohols such as propanol, butanol or pentanol (all isomeric forms). Raw materials are frequently used that contain alcohol mixtures. These may have, for example, a certain percentage (e.g. at least 10% by weight, preferably at least 20% by weight, more preferably at least 50% by weight) of ethanol, based on the weight of the alcohols, however they may also be ethanol-free. Preferably $C_2$-$C_4$ alcohols are considered as alcohols.

The reaction occurs at 300° C., preferably at least 350° C., particularly in the case of the reaction of ethanol. It is likewise preferable not to exceed the upper limit of 600° C. The minimum pressure should be about 220 bar ($2.2 \times 10^7$ Pa). The pressure and temperature should be selected such that the alcoholic initial solution achieves its supercritical state and the mixture maintains this state even throughout the modification of the relation of water to alcohol through the reaction of alcohol to olefin. Depending on the alcohol concentration, temperatures of 350° C. or more are beneficial, preferably 400° C. or more, respectively at pressures of 250 bar or more.

The initial concentration of alcohol in the aqueous solution may vary in a broad range, which preferably comprises 5 to 95% by volume. The inventors found that raw materials even with just a relatively low concentration of alcohols can be reacted well, e.g. in the range of 10 to 500 g/l, particularly preferably in the range of 15 to 300 g/l.

The water content of the solution is not critical and may fluctuate widely. However, it must be noted that it may potentially be relatively low because catalytic quantities are already sufficient. Normally, however, it should constitute at least 1 or preferably 2% of the solution by weight. The aqueous alcohol solution may also contain further liquid (dissolved) components containing carbon such as organic acids, which may be, for example, by-products of a fermentative or petrochemical pre-reaction. In this regard, the nature of these components as well as the total carbon content in the solution is not limited.

The contact time of the alcohol with the catalyst and thus the retention time under the specified conditions can be selected according to need depending on the initial concentration or the catalyst selected. Surprisingly, it has been found that time periods are fully sufficient in the second or minute range, e.g. 5 to 300 seconds. Lower concentrations tend to shorten the retention time even further, such that the process can be performed with contact/retention times of usually no more than 100 seconds, wherein simultaneously superior results can be observed both in terms of total yield as well as specificity. Retention times of 10 to 80 seconds particularly beneficial, including particularly preferably from 20 to 35 seconds, and particularly in combination with the aforementioned pressures and/or temperatures. The particular aim of this short retention time is that the process can be designed as a continuous process with a high throughput.

The gas and liquid phase is preferably separated while still under pressure. Thus, after the reaction, the olefin is still under pressure and can be further reacted or filled.

If residual alcohol and potentially formed dialkyl ether remained in the liquid phase, the product flow for achieving a further improved yield may be returned to the reactor, for example in the form of an admixture to new raw material.

The process pursuant to the invention is particularly suitable for recycling biomaterials treated through fermentation or alcoholic solutions that arise in the chemical industry (e.g. in the petrochemical industry). Potentially existing solids, such cellulosic materials, should be separated in advance to avoid an unnecessary carbonization and thus deactivation of the catalyst. The means of choice for this is frequently single-stage evaporation (flash distillation). Dissolved salts usually do not interfere as long as an acidic pH value is set under the reaction conditions; however they essentially do not transfer in single-stage evaporation. In this regard, the process pursuant to the invention has a distinct advantage over the previously common gas-phase dehydration as this requires the initial mixture to be purified through complex rectification.

Compared to classical dehydration in the gas phase, the invention has the following benefits:
  Eliminating the multistage rectification for concentration of alcohols produced through fermentation
  Improving the space-time yield due to the reaction in a condensed phase
  Reduced process energy requirement as no evaporation is necessary; merely heating
  The olefin is available under high pressure after the reaction—eliminating gas compression
  Elimination of transportation and storage costs for, e.g. ethylene, as it can be produced directly at the consumer (e.g. in proximity to production facilities that do not have a pipeline network and thus have no direct access to, e.g. ethylene or propylene).
  The developed process may be implemented in small systems such that a pipeline connection is not necessary.

The experiments of the inventors of the present application with liquid acids led to results that are partially diametrically opposed to the results of literature—at least they were not to be expected—especially in view of the ratio of yield and specificity (see e.g. Example 2 (not that depicting the invention), accordingly, sulfuric acid as catalyst has a substantially lower specificity for the conversion of ethanol than for the conversion of published propanol). In this case, the problem discussed in the state of the art involving the aggressiveness of sulfuric acid and its effect on the container walls could possibly play a major role. As Watanabe et al. studied the dehydration of propanol with liquid acid as well as with solid oxides and the results were achieved slightly worse than those with acids when using solid catalysts, we could not have expected that the dehydration of the "hard nut" ethanol would be successful on acidic solid catalysts. However, the inventors of the present invention found that the ethanol yield is approximately equal and very high in any event when using sulfuric acid and solid catalysts, however the specificity—and thus the selective yield of ethylene— increases by more than 10-fold when using aluminum oxide. Moreover, they found that reaction conditions with pressures/temperatures clearly in the supercritical range, e.g. temperatures of 380° C. and/or pressures of 240 bar, significantly increase the yield, while selectivity decreases somewhat.

The yield can be further increased if zirconium oxide or titanium dioxide is used instead of aluminum oxide. The use of acid-modified catalysts creates high ethylene selectivity.

These results were completely surprising. First, this knowledge enables a successful dehydration in the form of a continuous process on a fixed-bed catalyst.

In a preferred way, the reaction progresses as follows, wherein a system diagram suitable for this is shown in FIG. 1: An aqueous alcoholic solutions, which was attained, is first through fermentation or petrochemical processes, is first condensed from a receiver, such as receiver tank 1 by means of a pump (in this case high-pressure pump 2) to at least 220 bar or one of the aforementioned preferable pressure ranges. The solution is brought to temperatures between preferably 350 to 600° C., which can be achieved with the aid of counter-current heat exchanger 3 and/or superheater 4. To start the system, e.g. bypass 5 may be used. The supercritical reaction solution is reacted in reactor 6, which can be operated adiabatically or isothermally, on a catalyst fixed bed, e.g. a fill. Naturally, the use of a monolithic catalyst material would also be possible. Said catalyst fixed bed, normally as usually filled from a technical perspective, preferably fills the entire reactor volume. This has multiple benefits. First, an even flow of the reactor is achieved in this manner. Second, the reaction solution is exposed to contact with the catalyst under the pressure and temperature conditions prevailing there during the entire retention time in the reactor.

Alternatively, for example, a reactor cascade for increasing selectivity may be used. The retention time in the reactor in this case is preferably 5 to 300 seconds. As a catalyst, the aforementioned catalysts may be used, potentially even as mixtures or acid-modified carrier materials. After leaving the reactor portion, the product flow is preferably placed in cooler 7, in a favorable manner above the specified counter-current heat exchanger. Cooling occurs in said cooler, e.g. at below 50° C., wherein however the pressure is maintained. From the cooler, the two-stage mixture is lead to separator 8, in which the mixture is separated into raw olefin gas phase 9 and aqueous liquid phase 10. Said gas phase may be subjected to an additional subsequent purification, as we are aware from the state of the art.

Figure 2:
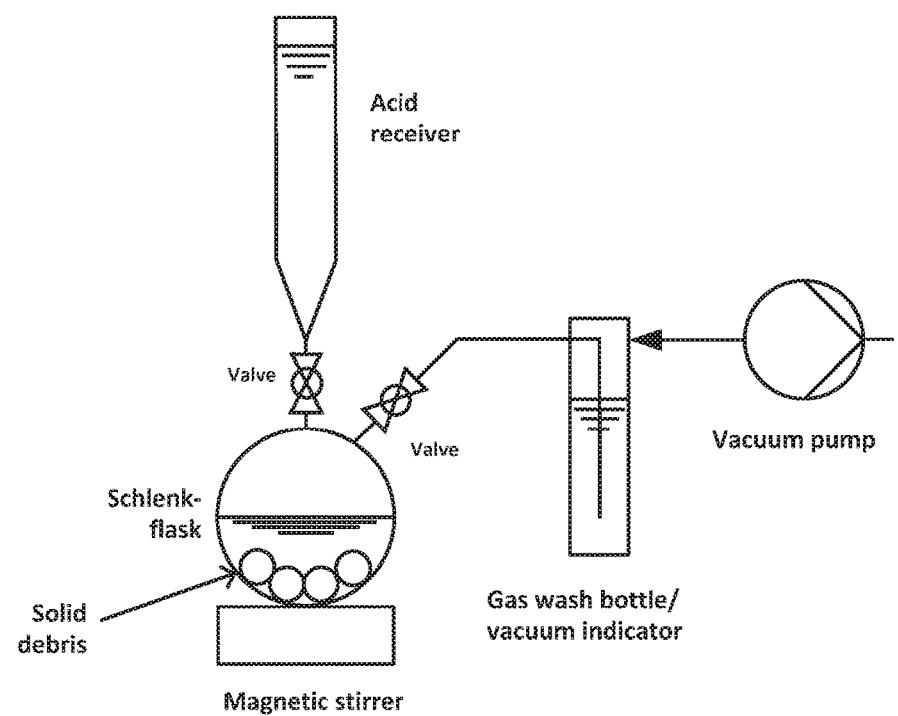
FIG. 2 is a diagram of a device which helps in the production of catalysts used in accordance with the present invention.

The aforementioned reaction was conducted to the following catalysts, etc., which were produced through a saturation process:
Cat 01 activated carbon+$H_2SO_4$ (calcined in a nitrogen atmosphere)
Cat 02 activated carbon+$H_3PO_4$ (calcined in a nitrogen atmosphere)
Cat 03 $Al_2O_3$+$H_2SO_4$
Cat 04 $Al_2O_3$+$H_3PO_4$
Cat 05 $TiO_2$+$H_2SO_4$ Cat 06 TiO$_2$+H$_3$PO$_4$
Cat 07 ZrO$_2$+H$_2$SO$_4$
Cat 08 ZrO$_2$+H$_3$PO$_4$ These catalysts can be produced, for example, according to the process described in the following and/or with the help of the device depicted in FIG. 2. In this regard, a flask (in this case a Schlenk flask) is evacuated with a vacuum pump to ensure that all capillary oxygen was removed from the catalyst material prior to saturating the solid with acid. A gas-wash bottle filled with water serves as a vacuum indicator. If the formation of gas bubbles on the immersion tube of the gas-wash bottle decreases, we can ensure that the maximum possible vacuum has been achieved. Furthermore, the water bath prohibits the discharge of the smallest particles. After achieving the vacuum, the acid receiver can be put into the reaction container; the vacuum should be kept there. By dispersing the catalyst solid in sulfuric acid (e.g. 1N) or phosphoric acid (e.g. 1N), active sulfuric or phosphoric acid centers are produced on the surfaces of the particles. After an exposure period, which may be, e.g. between 0.5 and 2 hours and preferably approx. 1 hour, the vacuum can be removed and the content of the flask emptied via a filter (e.g. a blue ribbon filter). The filter residue is dried, e.g. for 24 hours at approx. 105° C. in a drying chamber, and subsequently calcined, for example, for 24 hours at 500° C.

For producing metallic and semi-metallic phosphates, the respective metallic or semi-metallic compounds, e.g. oxides, acids, chlorides or oxychlorides are reacted with phosphoric acid. Examples for suitable cations are titanium, zirconium, and aluminum. For this purpose, approx. 5 to 50 g of the respective metallic or semi-metallic compound can favorably be weighed in and transferred to a reaction container for reactions on a laboratory scale. For this, a super-stoichiometric mass of 85% orthophosphoric acid (or another phosphoric acid) is added and de-ionized water (preferably in a quantity of no more than 50% of the phosphoric acid) is additionally provided to the reaction mixture for an improved homogeneity and ability to mix thoroughly. The reaction container and the reaction mixture differ for exothermic and endothermic reactions. Endothermic reactions are conducted in a heated round-bottom flask in a boiling state with reflux cooling; exothermic reactions are conducted in a cooled beaker. The boiling temperature is between approx. 90° C. and 110° C. The duration of the reaction for the chemical reaction to the phosphates in this case is favorably respectively approx. 4 hours in the selected temperature range.

Following completion of the reaction period, the solutions are tempered to room temperature. Depending on the type of anion of the reactant, a second reaction may be necessary for neutralizing resulting inorganic acid and simultaneous precipitation of the phosphate. For example, hydrochloric acid arising when using a raw material containing chloride is neutralized with NaOH. Subsequently, the product is vacuum filtered, e.g. via a filter for minute precipitations. A blue ribbon filter is preferably used in this regard.

Surface water is removed from the filter residue obtained in this manner, e.g. in a drying chamber at 105° C. for 24 hours. The phosphate is preferably subsequently calcined, e.g. in a muffle furnace at an elevated temperature. In the process, capillary water and water of crystallization is removed, through which the catalyst achieves its activity. Based on measurements of the specific surface area and its correlation to the catalytic activity, a temperature range between approx. 300° C. and 1100° C. proved to be particularly beneficial for this. The quality of the catalyst preparation can be, e.g. gravimetrically determined. Even the percentage of the coating of the surface with acidic groups can be determined relative to the maximum possible coating. The material often becoming lumpy during calcinations is subsequently reduced to small pieces in a mortar.

In the following, the invention will be explained in further depth based on examples.

EXAMPLE 1 (COMPARISON EXAMPLE)

In a system, as depicted in FIG. 1, the reactor was completely filled with 150 ml of SiC as a carrier material in order to achieve a constant flow profile. As a raw material, a 25% ethanol solution was reacted in water at a reaction temperature of 400° C. and a pressure of 250 bar. The retention time in the reactor was 20 seconds. In this process, a yield of 21.8% was achieved with an ethylene selectivity of 29.7%.

EXAMPLE 2 (COMPARISON EXAMPLE)

Example 1 was repeated with the modification that a few drops of 98% sulfuric acid by weight were added to the ethanol solution in the reactor. In this process, a yield of 89.7% was achieved with an ethylene selectivity of 6.8%.

EXAMPLE 3

Example 1 was repeated with the modification that the reactor contained γ-Al$_2$O$_3$ pellets instead of SiC as a carrier material. In this process, a yield of 23.3% was achieved with an ethylene selectivity of 91.5%.

EXAMPLE 4

Example 3 was repeated with the modification that the retention time was 30 seconds. In this process, a yield of 92.5% was achieved with an ethylene selectivity of 97.6%.

EXAMPLE 5

In a system, as depicted in FIG. 1, the reactor was filled with 44 ml of ZrO$_2$ (tetragonal) as a catalyst material. As a raw material, a 39% ethanol solution was reacted in water at a reaction temperature of 357° C. and a pressure of 230 bar. The retention time in the reactor was 64 seconds. In this process, a yield of 56.7% was achieved with an ethylene selectivity of 73.8%.

EXAMPLE 6

In a system, as depicted in FIG. 1, the reactor was filled with 28 ml of γ-Al$_2$O$_3$ as a catalyst material. As a raw material, a 39% ethanol solution was reacted in water at a reaction temperature of 357° C. and a pressure of 230 bar. The retention time in the reactor was 75 seconds. In this process, a yield of 47.9% was achieved with an ethylene selectivity of 70.4%.

EXAMPLE 7

In a system, as depicted in FIG. 1, the reactor was filled with 33 ml of TiO$_2$ (anatase) as a catalyst material. As a raw material, a 39% ethanol solution was reacted in water at a reaction temperature of 357° C. and a pressure of 230 bar.

The retention time in the reactor was 72 seconds. In this process, a yield of 87.9% was achieved with an ethylene selectivity of 11.5%.

What is claimed is:

1. A process for the continuous production of olefins comprising:
   a) Providing a solid-free aqueous solution comprising an alcohol selected from the group comprising ethanol, propanol and butanol;
   b) Directing said solid-free aqueous solution to a reactor comprising a fixed-bed catalyst;
   c) Contacting said solution with the catalyst in supercritical conditions of a mixture containing water, said alcohols and said olefins, the supercritical conditions comprising a temperature of at least 300° C., a pressure of at least 220 bar, and a retention time between 5 and 300 seconds, thereby producing an effluent mixture; and
   d) Separating the effluent mixture into a raw olefin gas phase and an aqueous liquid phase;
   e) Wherein the catalyst is selected from the group consisting of Periodic Table group three metal oxides, secondary group four metal oxides, secondary group six metal oxides, insoluble metallic phosphates, insoluble semi-metallic phosphates, porous pumice coated with an inorganic acid group, and carbon coated with an inorganic acid group.

2. The process according to claim 1, wherein the retention time of said solution in said reactor is between 5 and 100 seconds.

3. The process according to one of the claim 1, wherein said reactor is completely filled with said catalyst.

4. The process according to claim 1, wherein said fixed-bed catalyst is selected from among oxides of cations of the third main group as well as the fourth to sixth secondary group of the periodic table, the surface area of which is coated with inorganic acid groups.

5. The process according to claim 1, wherein said fixed-bed catalyst is selected from among oxides of aluminum, zirconium, and titanium, porous materials selected from among pumice and carbon, the surface area of which is coated with sulfate or phosphate groups and metal phosphates.

6. The process according to claim 1, wherein said fixed-bed catalyst is selected from among aluminum phosphate, zirconium phosphate, phosphated aluminum oxide, phosphated titanium oxide, phosphated zirconium oxide, phosphated carbon, phosphated pumice, sulfated zirconium oxide, sulfated titanium oxide, sulfated carbon, sulfated pumice, and sulfated aluminum oxide.

7. The process according to claim 1, wherein said aqueous solution of the alcohols has ethanol, propanol or butanol as a single alcohol or as one of the alcohols in a quantity of at least 10% by weight in relation to the overall weight of available alcohols.

8. The process according to claim 1, wherein said aqueous solution of the alcohols has ethanol as a single alcohol or as one of the alcohols in a quantity of at least 10%-by weight in relation to the overall weight of the alcohols.

9. The process according to claim 1, wherein said temperature is at least 350° C. and/or said pressure is 250 bar or more.

10. The process according to claim 1, wherein an initial concentration of alcohols in said aqueous solution is 5 to 95% (wt./vol.).

11. The process according to claim 1, wherein said aqueous solution is cooled after leaving the reactor containing said fixed-bed catalyst while still under pressure, whereupon a gas and liquid phase is separated such that the resulting olefin continues to remain under pressure.

12. The process according to claim 1, wherein said resulting aqueous liquid phase is mixed with a new solution of said alcohols after being separated from the raw olefin gas phase and is in turn led to the reactor together with it, wherein the retention time of said solution in the reactor is between 5 and 100 seconds.

13. The process according to claim 1, wherein a solution is used as an alcoholic aqueous solution, which was obtained from biomaterials or materials containing alcohol treated through fermentation that arise in the chemical industry.

14. The process according to claim 1, wherein said aqueous alcoholic solution is heated with the help of a counter-current heat exchanger, in which the alcoholic solution is guided in counter-flow to a solution leaving the reactor.

15. The process according to claim 2, wherein the retention time of said solution in said reactor is between 10 and 80 seconds.

16. The process according to claim 8, wherein said aqueous solution of the alcohols has ethanol as a single alcohol or as one of the alcohols in a quantity of at least 20% by weight in relation to the overall weight of available alcohols.

17. The process according to claim 9, wherein said temperature is 400° C. or more and/or said pressure is 250 bar or more.

18. The process according to claim 10, wherein an initial concentration of alcohols in said aqueous solution is 15 to 30% (wt./vol.).

19. The process according to claim 12, wherein the retention time of said solution in the reactor is between 10 and 80 seconds.

* * * * *